US006627432B2

(12) United States Patent

Farina et al.

(10) Patent No.: US 6,627,432 B2

(45) Date of Patent: Sep. 30, 2003

(54) LIQUID FLOW AND CONTROL IN A BIOLOGICAL TEST ARRAY

(75) Inventors: Edward Francis Farina, Oxford, PA (US); Samuel Garfield Ferguson, Jr., Bear, DE (US); Peter Louis Gebrian, Wilmington, DE (US); Frank Stephen Krufka, Kirkwood, PA (US); John Charles Mazza, Newark, DE (US); Nicholas Michael Shmel, Jr., Elkton, MD (US)

(73) Assignee: Dade Behring Inc., Deerfield, IL (US)

( * ) Notice: Subject to any disclaimer, the term of this patent is extended or adjusted under 35 U.S.C. 154(b) by 275 days.

(21) Appl. No.: 09/795,823

(22) Filed: Feb. 28, 2001

(65) Prior Publication Data

US 2002/0119561 A1 Aug. 29, 2002

(51) Int. Cl.[7] ................................................ C12M 1/34

(52) U.S. Cl. ............................... 435/288.5; 435/287.3; 435/305.3; 435/33

(58) Field of Search ............................... 435/33, 286.5, 435/286.6, 287.3, 288.5, 288.7, 305.2, 305.3; 422/58, 61, 102

(56) References Cited

U.S. PATENT DOCUMENTS

| | | | | |
|---|---|---|---|---|
| 3,832,532 | A | 8/1974 | Praglin et al. | |
| 4,018,652 | A | 4/1977 | Lanham et al. | |
| 4,077,845 | A | 3/1978 | Johnson | |
| 4,704,255 | A | 11/1987 | Jolley | 422/102 |
| 5,589,350 | A | 12/1996 | Bochner | |
| 5,609,828 | A | 3/1997 | O'Bear et al. | 422/102 |
| 5,679,310 | A | 10/1997 | Manns | 422/102 |
| 5,746,980 | A | 5/1998 | O'Bear et al. | 422/102 |
| 5,766,553 | A | 6/1998 | Staples et al. | 422/102 |
| 5,922,593 | A | 7/1999 | Livingstron | 435/288.5 |
| 5,932,177 | A | 8/1999 | O'Bear et al. | 422/102 |

*Primary Examiner*—William H. Beisner

(74) *Attorney, Agent, or Firm*—Leland K Jordan

(57) ABSTRACT

A microbiological test array with a generally flat base having a plurality of upwardly projecting microwells connected by a microchannel to an open reservoir formed in a top surface generally parallel to the base of the test array. The reservoir has an opening to permit an inoculum-broth liquid solution to flow from the reservoir through the microchannel, to a sacrificial evaporation well having an air vent port adapted to control a vacuum filling process, and subsequently to be distributed into each of the plurality of microwells.

10 Claims, 8 Drawing Sheets

LIQUID FLOW AND CONTROL IN A BIOLOGICAL TEST ARRAY

FIELD OF THE INVENTION

The present invention relates to microbiological test arrays suitable for use in automated analyzers employing a carrier to transport such arrays between various functional stations. More particularly, the present invention provides a test array having a sealable vacuum port to facilitate control of a flow of a liquid solution from a reservoir on the array to a number of microwells on the array and a sacrificial well to protect the integrity of the solution within the microwells.

BACKGROUND OF THE INVENTION

Various types of tests related to patient diagnosis and therapy can be performed by analysis of a biological sample. Biological samples containing the patient's microorganisms are taken from a patient's infections, bodily fluids or abscesses and are typically placed in test panels or arrays, combined with various reagents, incubated, and analyzed to aid in treatment of the patient. Automated biochemical analyzers have been developed to meet the needs of health care facilities and other institutions to facilitate analysis of patient samples and to improve the accuracy and reliability of assay results when compared to analysis using manual operations. However, with ever changing bacterial genera and newly discovered antibiotics, the demand for biochemical testing has increased in both complexity and in volume. Because of these greater demands in conjunction with the expense and scarcity of floor space within health care institutions and the pressure to provide clinical results at lower costs, it has become important to simultaneously perform various types of biochemical tests within a highly automated and compact analyzer that operates with minimal clinician attention using cost-effective techniques.

An important family of automated microbiological analyzers function as a diagnostic tool for determining both the identity of an infecting microorganism and of an antibiotic effective in controlling growth of the microorganism. In performing these test, identification and in vitro antimicrobic susceptibility patterns of microorganisms isolated from biological samples are ascertained. Such analyzers have historically placed selected biochemicals into a plurality of small sample test wells in panels or arrays that contain different growth media, or antimicrobics in serial dilutions. Identification (ID) of microorganisms and of Minimum Inhibitory Concentrations (MIC) of an antibiotic effective against the microorganism are determined by color changes, fluorescence changes, or the degree of cloudiness (turbidity) in the sample test wells created in the arrays. By examining the signal patterns generated, both MIC and ID measurements and subsequent analysis are performed by computer controlled microbiological analyzers to provide advantages in reproducibility, reduction in processing time, avoidance of transcription errors and standardization for all tests run in the laboratory.

In ID testing of a microorganism, a standardized dilution of the patient's microorganism sample, known as an inoculum, is first prepared in order to provide a bacterial or cellular suspension having a predetermined known concentration. This inoculum is placed in an analytical test array or panel having a number of microwells or alternately into a cuvette rotor assembly having an inoculum receiving well from where sample is distributed by centrifugal force to a number of test wells or chambers at the periphery of the rotor. The test wells contain identification media consisting of substrates and/or growth inhibitors, which, depending on the species of microorganism present, will exhibit color changes, increases in turbidity or changes in fluorescence after incubation. For instance, a bacterial genera may be identified on the basis of pH changes, its ability to utilize different carbon compounds, or growth in the presence of antimicrobial agents in a test well. Some tests require addition of reagents to detect products of bacterial metabolism while others are self-indicating. In conventional chromogenic panels, the inoculum is incubated some 18–24 hours before analysis is completed. Alternately, microorganism ID may be accomplished using rapid fluorogenic test arrays employing growth-independent means in which a preformed enzyme substrate is placed in the test wells and fluorogenic tests based on the detection of hydrolysis of fluorogenic substrates, pH changes following substrate utilization, production of specific metabolic substrates and the rate of production of specific metabolic byproducts are made after about 2 hours of incubation. In both cases, by examining the reaction of the inoculum and reagents after incubation and over a period of time, or lack thereof, and comparing that reaction with that of known species, the types of microorganisms can be identified.

The use of microbiological test trays and the techniques employed in MIC tests, also known as antibiotic susceptibility testing, AST, of microorganisms are also well known. AST tests are essentially broth dilution susceptibility tests using wells filled with inoculum and a growth broth, called herein a inoculum-broth solution, and increasing concentrations of a number of different antibiotics, or antimicrobial agents. The different antimicrobial agents are typically diluted in Mueller-Hinton broth with calcium and magnesium in chromogenic panels or diluted in autoclaved water with a fluorogenic compound in fluorogenic panels. The antimicrobials are diluted to concentrations that include those of clinical interest. After incubation, the turbidity or fluorescence will be less or non-existent in wells where growth has been inhibited by the antimicrobics in those wells. The analyzer compares each test well reading with a threshold value. The threshold value is a fixed number corresponding to a certain percentage of relative absorbency or fluorescence which corresponds to clinically significant growth. The MIC of each antimicrobial agent is measured either directly as visible growth, or indirectly as an increase in fluorescence.

Important challenges that must be taken into consideration when designing cost-effective, automated biochemical analyzers include the volume of reagents required per test and the cost of the disposable test panel, array or, in certain designs, a centrifugal test rotor. Because they are small and may be produced using mass-production, plastic injection molding techniques, it is advantageous to use very small sized, test arrays like those of the present invention having a number of microwells for performing AST tests in order to facilitate automatic handling and minimize the expense of a disposable test array. AST test arrays typically consist of a plurality of adjacent microwells aligned in some sort of an array that function as reaction vessels for the above mentioned biochemical reactions involving a solid phase media and a liquid phase containing a sample to be tested. An aliquot of the sample is placed in each microwell along with appropriate antibiotic reagents. AST testing usually requires that the test trays be incubated at a controlled temperature for a period of time so that an observable reaction between the sample and reagent occurs; at predetermined time intervals, each microwell of the test tray is examined for an indication of changes in color change, turbidity, or size.

Filling the number of microwells with the required inoculum and/or reagents presents several technical challenges that are made increasingly difficult as the size of the microwells is reduced. These challenges include providing a uniformity of fill, maintaining an absence of air bubbles that impede test observations, controlling adverse evaporation effects, maintaining the integrity of test observations, etc. Efforts have been made to address these challenges along with other problems and these generally employ a vacuum technique in filling microwells within a test array via an interconnected number of micro-sized channels connected between the microwells and an inoculum reservoir.

U.S. Pat. No. 5,932,177 provides a test sample card as typically used in biochemical analysis, having a number of same-sized rectangular shaped sample wells and fluid flow by means of a plurality of through-channels which route the fluid flow of samples along both the front and back surfaces of the card. Elevated bubble traps are provided, as are integral interrupt slots for sensing card position and alignment.

U.S. Pat. No. 5,922,593 discloses a microbiological test panel having a plurality of translucent cups extending from a first side of a planar surface, and a chassis having a plurality of open-ended tubes formed in the chassis. The chassis includes a plurality of raised passage walls on a second side of the planar surface that form passageways over the openings at the bottom ends of the tubes. One end of the passageway has an opening to allow an inoculum to flow through the passageway. The chassis further comprises an air communication port formed as an open-ended tube extending from the second side of the planar surface.

U.S. Pat. No. 5,766,553 discloses a molded test sample card comprising a fluid entrance port and first and second end regions and first and second side regions. A plurality of growth or reaction wells are located in the card body between the first and second end regions and the first and second side regions. A fluid channel network connects the fluid entrance port to said growth wells. To improve the flow of the material during the molding process, cored regions are disposed in at least one of the first and second end regions or the first and second side regions.

U.S. Pat. No. 5,746,980 discloses a test sample card with a fluid intake port and sample wells disposed between its opposite surfaces. A fluid channel network connects the fluid intake port to the sample wells and a bubble trap is connected to at least one of the sample wells by a conduit with formed in said first surface of the card. The bubble trap is formed as a depression extending part way through the card body and is covered by sealant tape.

U.S. Pat. No. 5,679,310 discloses a microtiter plate formed of a substantially rigid, polymeric plate having a substantially flat upper surface and a array of cylindrical or frusto-conical wells. The well bottom is either fluid impervious or pervious. In embodiments with fluid pervious well bottoms, a vacuum plenum is provided below the wells for drawing fluid from the wells through the pervious material.

U.S. Pat. No. 5,609,828 discloses a sample card with an intake port and a first fluid flow distribution channel connected to the intake port to distribute a fluid sample from the intake port to a first group of sample wells and a second fluid flow distribution channel to distribute a fluid sample from the intake port to a second group of wells.

U.S. Pat. No. 4,704,255 discloses an assay cartridge which has a substantially rectangular base plate, a substantially rectangular top plate, and four sidewalls. The top plate has a plurality of reaction wells on its top side. A port through the base plate allows reducing the pressure in the waste reservoir relative to the pressure over the wells to draw the liquid phase of a reaction from the well through the filter and into the waste reservoir.

From this discussion, it may be seen that there remains a need for a test tray that simply and inexpensively solves the above described technical challenges. In particular, there is a need for a simple and inexpensive microbiological test array in which all the test wells contained therein may be easily and conveniently filled with a microbiological sample for AST testing without introducing complicated filling steps. There is a further need for a simple microbiological test array adapted to minimize adverse effects of air bubbles within a test solution during optical testing. There is an even further need for a simple microbiological test array in which the integrity of test solution in a filled microwell may be maintained against adverse evaporation effects.

SUMMARY OF THE INVENTION

The present invention meets the foregoing needs by providing a microbiological test array having a plurality of microwells prefilled with known amounts of different antibiotics that can be easily and conveniently filled with sample and used for AST testing. One particular embodiment of the present invention is directed at a microbiological test array with a generally flat lower surface base having a plurality of upwardly projecting microwells, each microwell having an flat upper ceiling, the microwells being connected by a single microchannel to an open reservoir formed in a upper surface top generally parallel to the base of the test array. The end of the reservoir nearest the microwells has an opening to permit an inoculum-broth liquid solution to flow from the reservoir through the microchannel, to a sacrificial evaporation well having an air vent port adapted to control a vacuum filling process, and subsequently to be distributed into each of the plurality of microwells. The air vent port remains open during an vacuum evacuation procedure and is closed thereafter. In an exemplary embodiment, the air vent port comprises a heat sealable opening formed in a meltable plastic material. The sacrificial evaporation well is provided as a non-tested reservoir from which inoculum-broth solution may evaporate to atmosphere thereby protecting the inoculum-broth solution in the test microwells. In order to minimize optical interference during testing, the central top of each microwell is provided with a smooth finish; in addition, each microwell is provided with an open upper edge portion opposite the flow of incoming inoculum-broth liquid solution so that air remaining within the microwell is effectively forced towards the open upper edge portion and away from its central top portion.

BRIEF DESCRIPTION OF THE DRAWINGS

These and other features and advantages of the present invention can best be understood by reference to the detailed description of the preferred embodiments set forth below taken with the drawings in which.

DETAILED DESCRIPTION OF THE PREFERRED EMBODIMENTS

Figure 1:
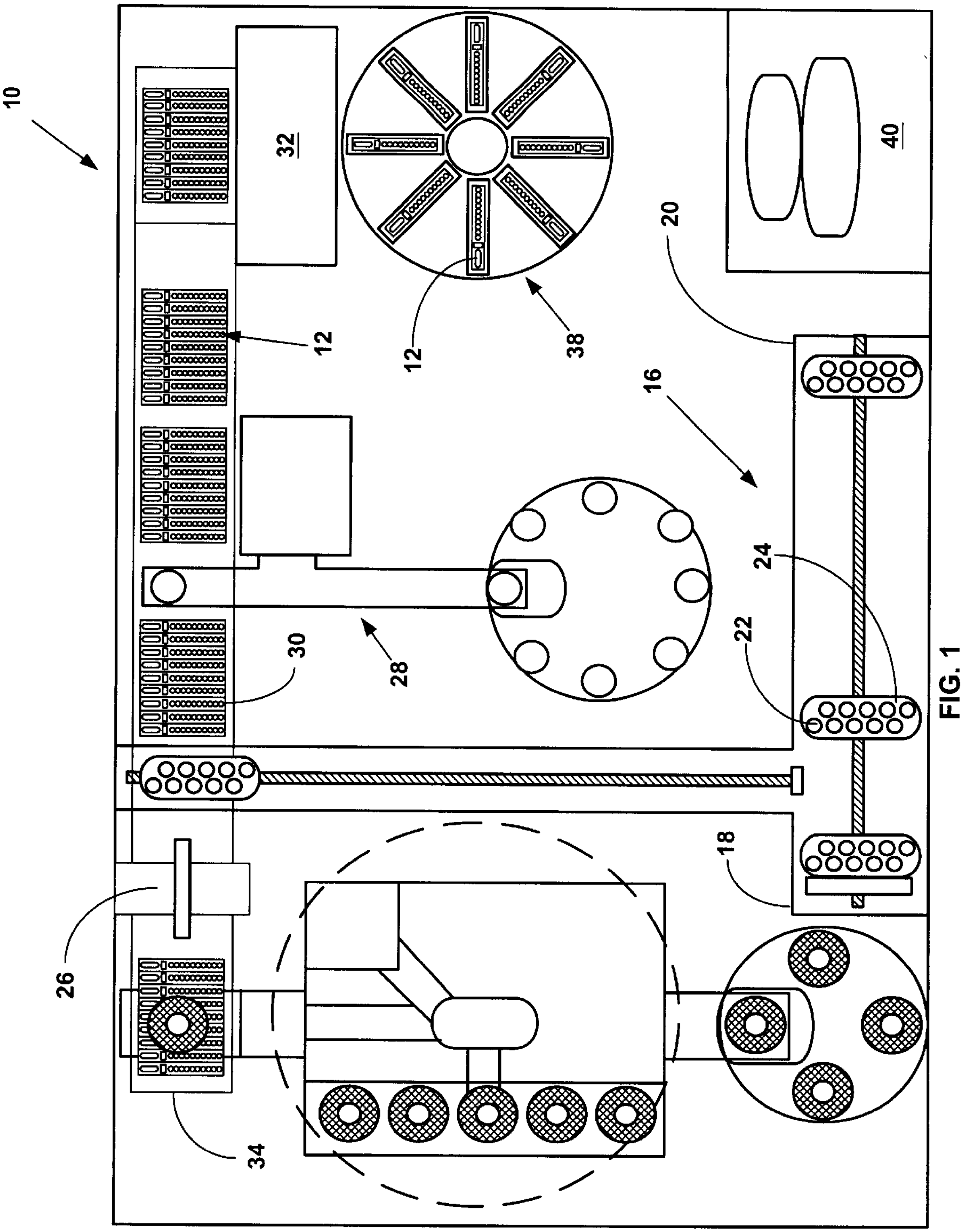
FIG. 1 is a simplified schematic plan view of an automated microbiological analyzer in which the test array of the present invention may be used.

FIG. 1 schematically illustrates a multifunctional automated microbiological analyzer 10 wherein the microwell test array 12 of the present invention may be used for receiving and storing reagents and for supporting biochemical reactions using test samples to be tested and analyzed. Antimicrobial Minimum Inhibitory Concentrations (MIC) also identified herein as Antibiotic Susceptibility Testing (AST) are determined by measuring color, fluorescence, or the degree of turbidity of a biochemical reaction between test samples and various antimicrobials which have been diluted to concentrations that include those of clinical interest and supplied to the different microwells within AST test array 12 during manufacture. An AST incubation and optical measuring station 14 may be adapted to conduct conventional AST tests using methods known in the art.

An AST microwell test array 12 may be transported throughout analyzer 10 using an automated transport system 16 having an input portion 18 and an output portion 20 located at the front of analyzer 10 for the various purposes described herein. Bi-directional arrows indicate the direction of movement along transport system 16. Transport system 16 comprises three separate segments adapted to transport test tubes 22 supported in a tube rack 24 and containing an inoculum of microorganisms isolated from biological specimens and having a bacteria concentration within a predetermined operable range. Transport system 16 moves each rack 24 to the rearmost portion of analyzer 10 where a translatable pipetting system 26 aspirates inoculum and dispenses a predetermined quantity of inoculum into a broth cup having a known solution of, for example, Mueller-Hinton broth. This inoculum-broth solution is mixed, aspirated and dispensed into a reservoir described hereinafter contained within an AST array 12 at an inoculum-broth dispensing station 28.

A number of AST arrays 12 may be carried using an AST array carrier 30 that is also transported by transport system 16 along the rearmost portion of analyzer 10 between the inoculum-broth dispensing station 28, an array carrier loading station 32, an AST array filling station 34, an AST array loading station 36 and an AST array disposal station (not shown). When an array carrier 30 is to be loaded at the array carrier loading station 32 with untested AST arrays 12, arrays 12 are moved to the carrier 30 by a feeding mechanism (not shown) from an AST array storage carousel 38 which contains a number of unfilled AST arrays 12. After a carrier 30 is fully loaded with unfilled AST arrays 12, the array carriers 30 are transported to the inoculum-broth dispensing station 28 where an amount of inoculum-broth solution is dispensed into an inoculum-broth solution receiving reservoir described hereinafter within each individual AST array 12; the arrays 12 are subsequently transported to the array filling station 34 where the inoculum-broth solution is dispersed uniformly to all test microwells in the individual arrays 12 using vacuum means described hereinafter.

Broth is supplied to the analyzer 10 in an appropriate container so that when an AST array 12 is to be filled with inoculum-broth solution, a known amount of inoculum is pipetted using translatable pipetting system 26 from a sample test tubes 22 into a broth container, mixed, and then aspirated from the broth container into the aforementioned inoculum-broth solution receiving reservoir 50 of individual test arrays 12.

After a number of individual AST microwells, described hereinafter and formed within AST test arrays 28, are loaded with inoculum-broth solution, AST arrays 12 are incubated at elevated temperatures for different lengths of time, depending upon test conditions, during which a number of test readings are conducted. Test readings may be obtained using any number of known means, including using optical methods in which light that has been passed through an interference filter is guided through the top of the AST microwells of the array 12 using lens or optical fiber channels. Light-sensitive photodiodes or the like detect the amount of light passing through each microwell and generate a electronic signal corresponding to the degree of turbidity within each. Antimicrobics are present in specified different concentrations in different microwells of AST test arrays 12. The turbidity will be less or non-existent in wells where growth has been inhibited by the antimicrobic. Thus, the intensity of light generated by a light source and captured by a detector after transmission through each microwell is inversely proportional to the concentration of bacteria in that well. Alternately, using a fluorometer system, the intensity of the fluoresence in each microwell is proportional to the concentration of bacteria in that well. In addition, selected microwells may contain biochemical substrates which exhibit a color change or fluoresence in the presence of certain bacteria. A calorimetric or fluorometric measurement, yields information about the solution in the well. The optical information generates a corresponding electrical signal which is then converted to computer-compatible digital form and stored in computer memory. The digital information is used by a Central Processing Unit (CPU) 40 having commands and control circuitry which are programmed to control all aspects of devices within analyzer 10. After a test array 12 has been optically analyzed and the values stored, each test well reading is compared with a threshold value corresponding to a certain percentage of relative absorbency or fluorescence which is found to correspond to clinically significant growth. These signals are then processed by the CPU 40 by comparing them to stored control values, thereby calculating the AST pattern. In this way, the MIC of each antimicrobic is determined.

Figure 2:
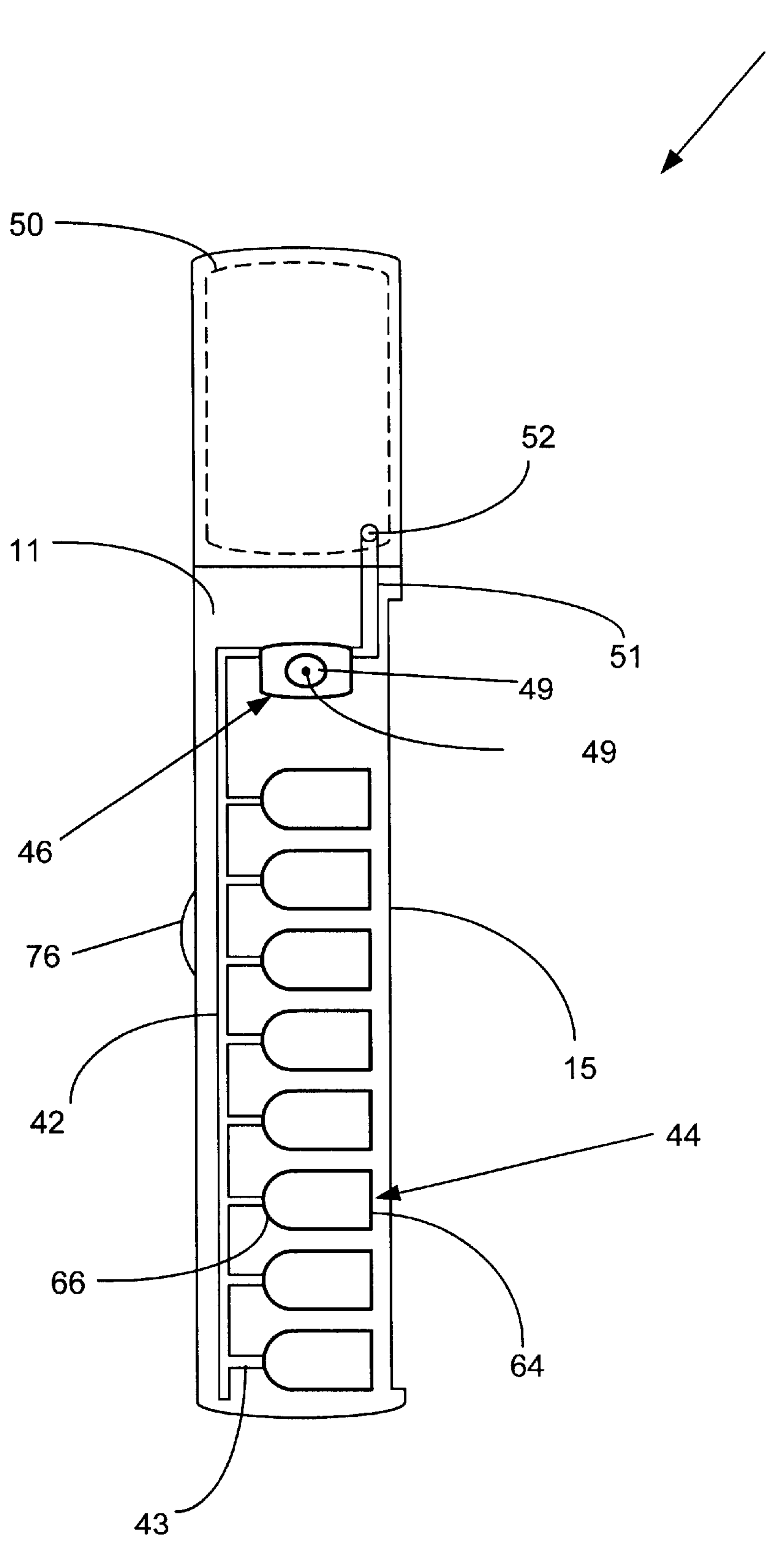
FIG. 2 is a bottom plan view of the test array of the present invention.
Figure 3:
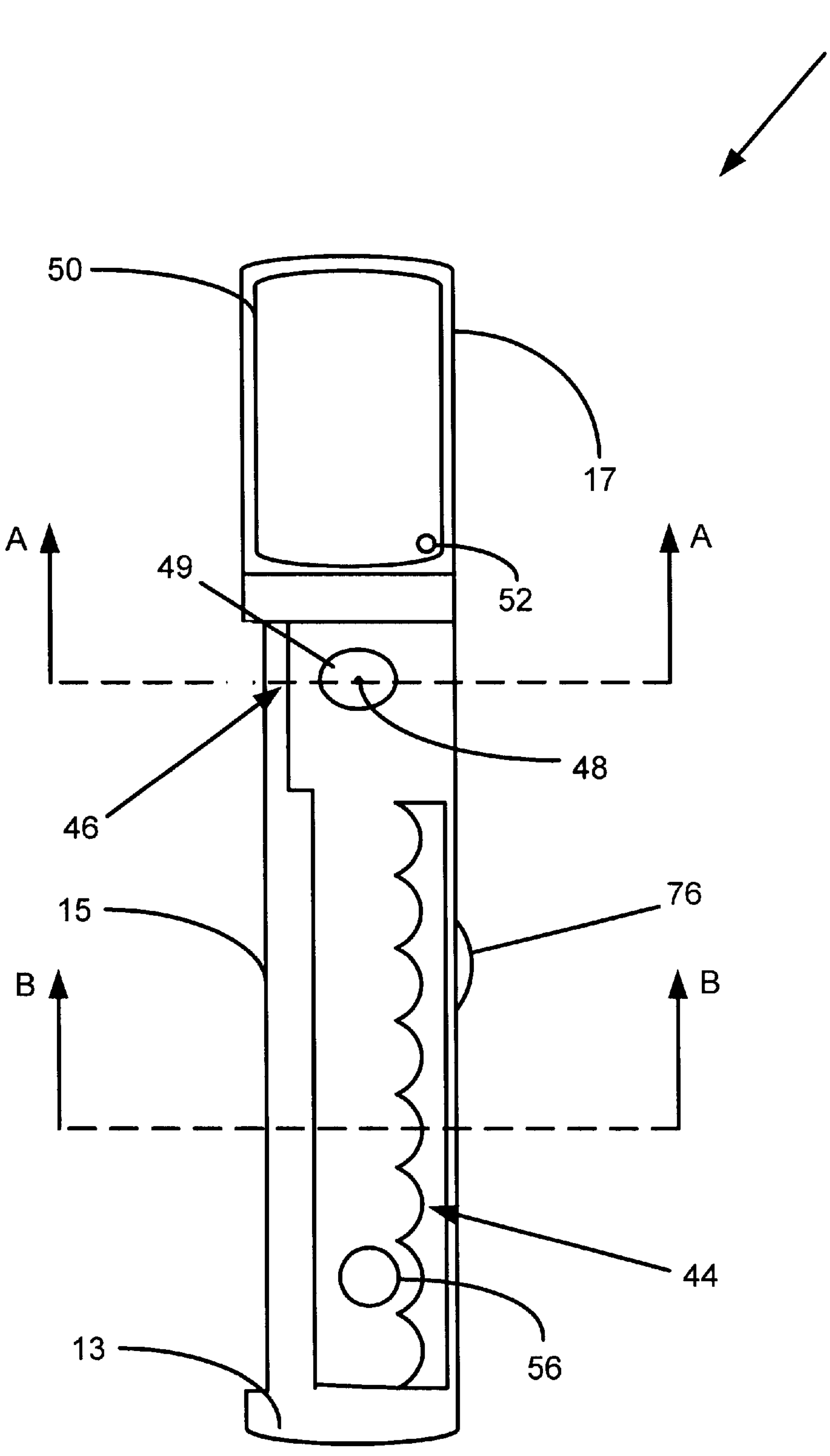
FIG. 3 is a top plan view of the test array of FIG. 2.
Figure 4:
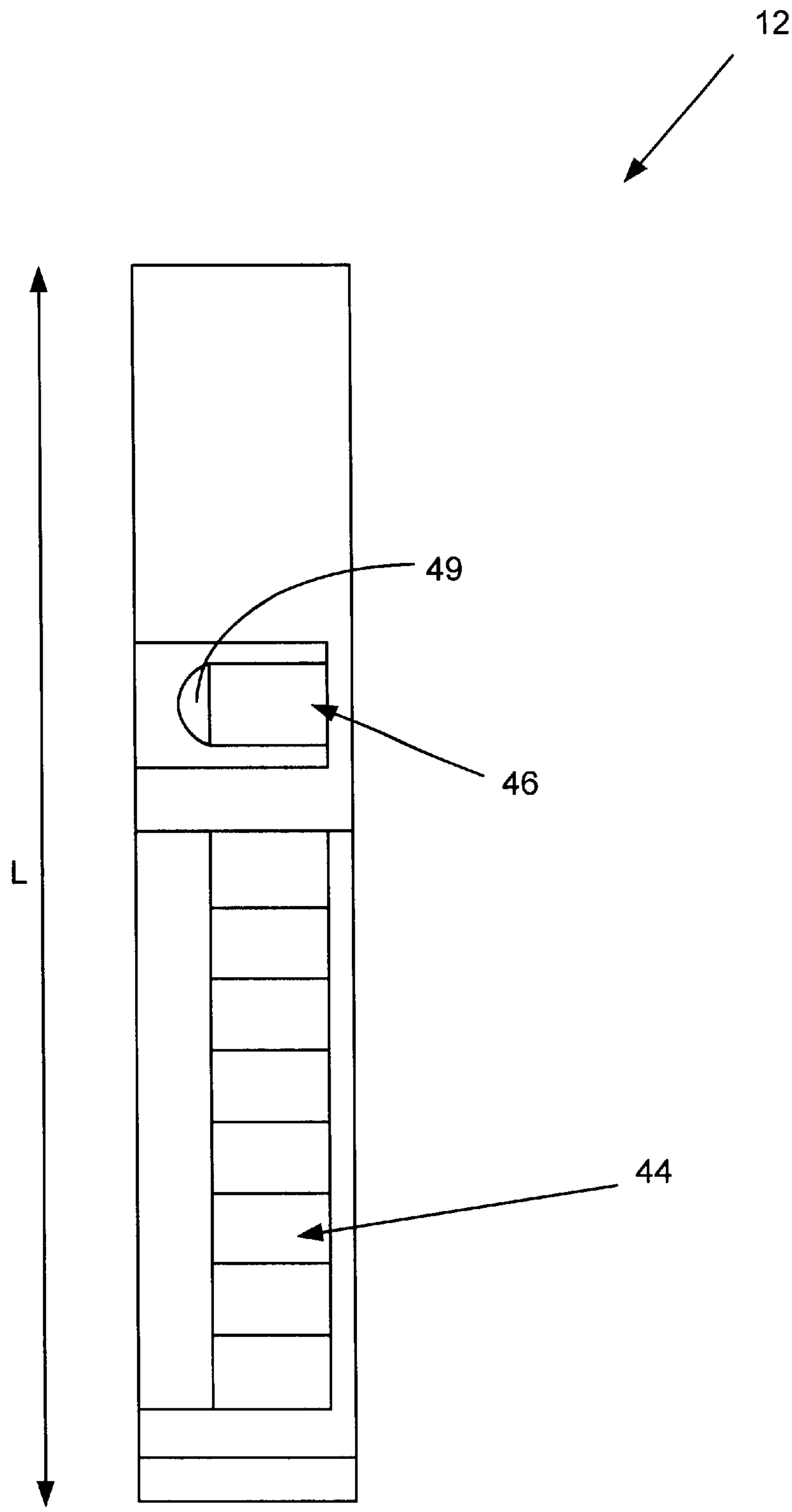
FIG. 4 is an elevational side view of the test array of the present invention.
Figure 5A:
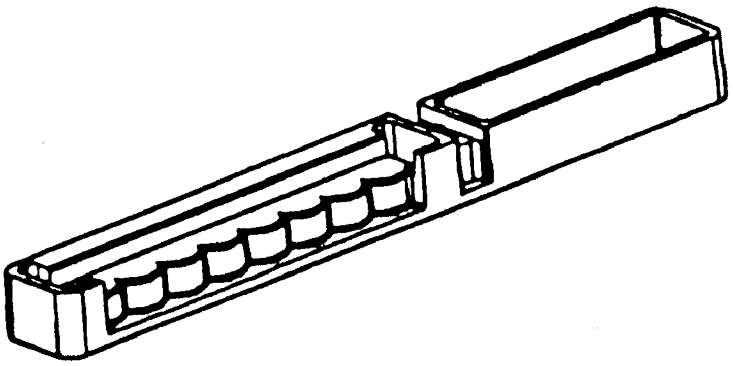
FIG. 5A is a perspective top view of the test array of the present invention.
Figure 5B:
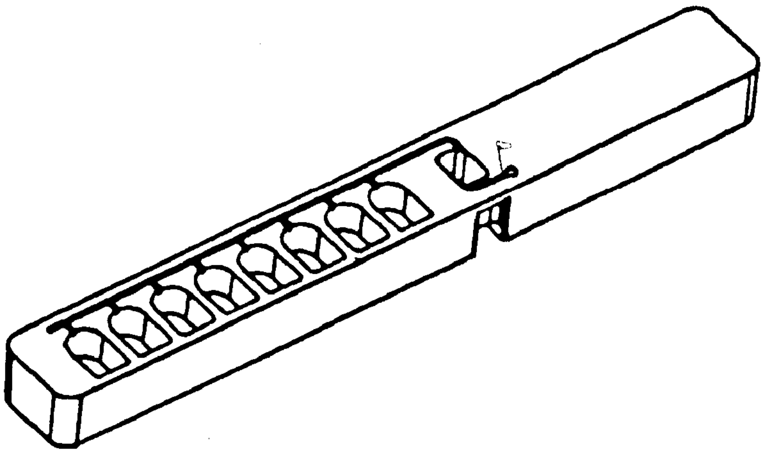
FIG. 5B is a perspective bottom view of the test array of the present invention; and, FIGS. 6A–6D are illustrative of a liquid filling process using the test array of the present invention.
Figure 6D:
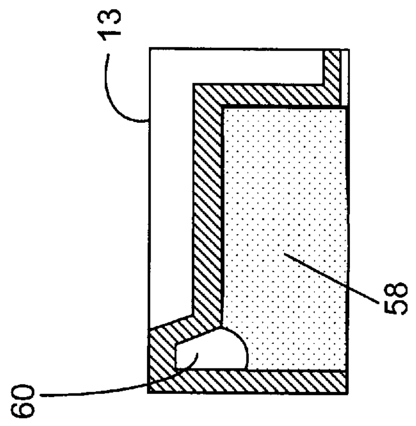
Figure 6C:
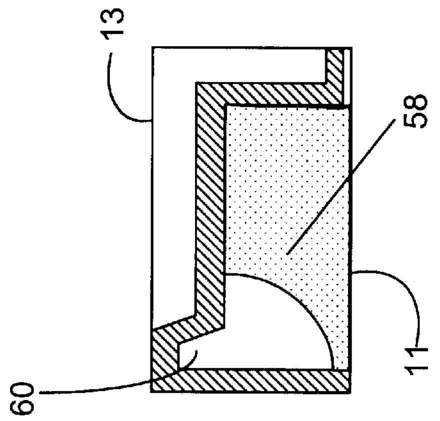
Figure 6B:
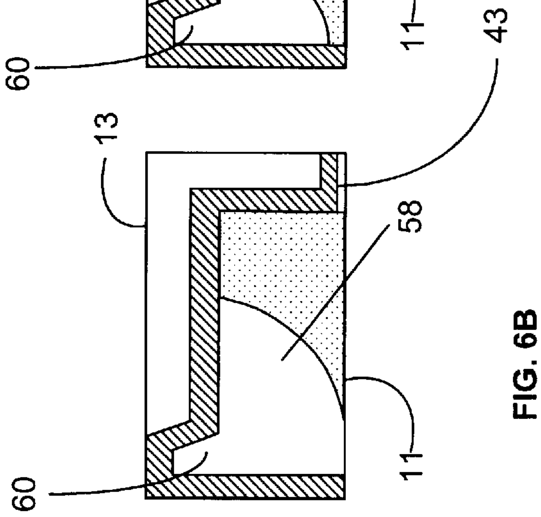
Figure 6A:
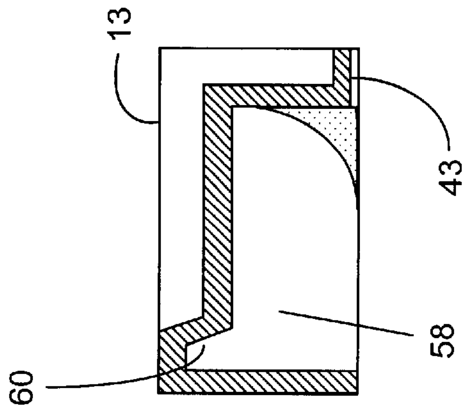

As seen in the embodiment of the present invention illustrated in FIG. 2 showing the lower bottom surface 11 of an AST array 12 as being relatively flat (see FIG. 5B), and in FIG. 3 showing the upper top surface 13 of the AST array 12 as containing relatively structured features described hereinafter (see FIG. 5B). Each AST array 12 has an elongate length L and a plurality of upwardly projecting microwells 44 formed in the bottom surface 11 as a linear row of single microwells 44 parallel to the length and is therefore of a generally elongate rectangular shape having the bottom surface 11 and top surface 13 on opposing sides, the opposed surfaces being separated by an indented sidewall 15 (see FIG. 5B) and an opposed second sidewall 17 (see FIG. 5A). Array 12 includes a plurality of upwardly projecting AST microwells 44 disposed in the bottom surface 11 along the elongate length L (FIG. 4) of the array 12 to form a single linear row of individual microwells 44. The individual microwells 44 are interconnected by a single microchannel 42 to a sacrificial evaporation well 46 formed in the bottom surface 11 of the test array upwardly projecting from an open portion of the bottom surface 11 and disposed between the row of microwells 44 and a reservoir 50 described hereinafter. The evaporation well 46 is also seen in FIG. 4 as having a closed dome-shaped upper surface 49 proximate the top surface 13 of the test array with a sealable vacuum port 48 formed therein as an opening in a dome-shaped upper surface 49 of the evaporation well 46 (FIG. 3, section A—A). Microwells 44 have the general shape of a closed well projecting upwards from the bottom surface 11 of the array 12 with a depth of about three-fourths the thickness of array 12, as illustrated in the perspective view FIG. 5A of the top surface 13 of array 12, and have openings along the bottom surface 11 of array 12, as illustrated in the perspective view FIG. 5B of the bottom surface 11 of array 12.

As seen in FIG. 2, microchannel 42 is formed as a open groove in the bottom surface 11 of the array 12 and connects the evaporation well 46 to a rectangular shaped inoculum-broth solution receiving reservoir 50 best seen in FIG. 3, the reservoir 50 having an open top and a closed bottom illustrated by dashed lines in FIG. 2. One end of the bottom of the reservoir 50 has a flow opening 52 also illustrated by dashed lines in FIG. 2, to allow an inoculum-broth solution dispensed into the top of reservoir 50 to flow from reservoir 50 through a short microchannel 41, firstly to the sacrificial evaporation well 46 and then through a longer microchannel 42 sequentially to each of the series of microwells 44. The open surface portions of microchannels 41 and 42, flow opening 52, sacrificial evaporation well 46, and microwells 44 along the bottom surface of array 12 may be closed by sealing over with a layer of adhesive tape (not shown) during a manufacturing process in which antimicrobics of clinical interest are placed in the different microwells 44 but not in the sacrificial evaporation well 46. Optionally, one well may be left empty of antimicrobics so that it may be used as a reference.

Figure 2A:
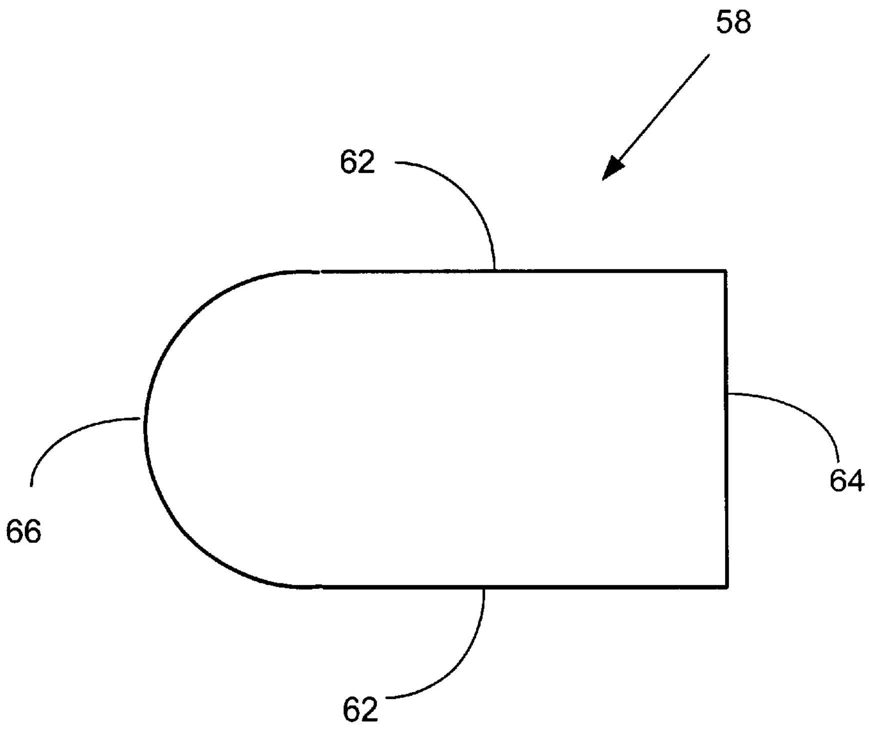
FIG. 2A is an enlarged bottom view of a portion of the test array of FIG. 2.
Figure 2B:
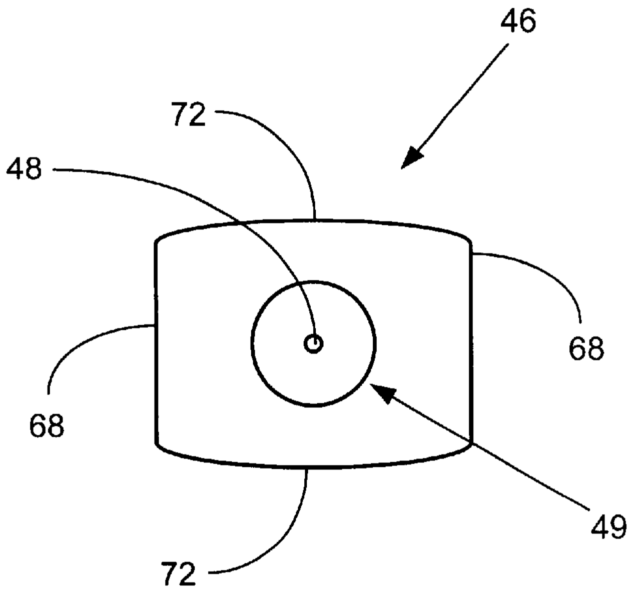
FIG. 2B is an enlarged bottom view of a portion of the test array of FIG. 2.
Figure 3A:
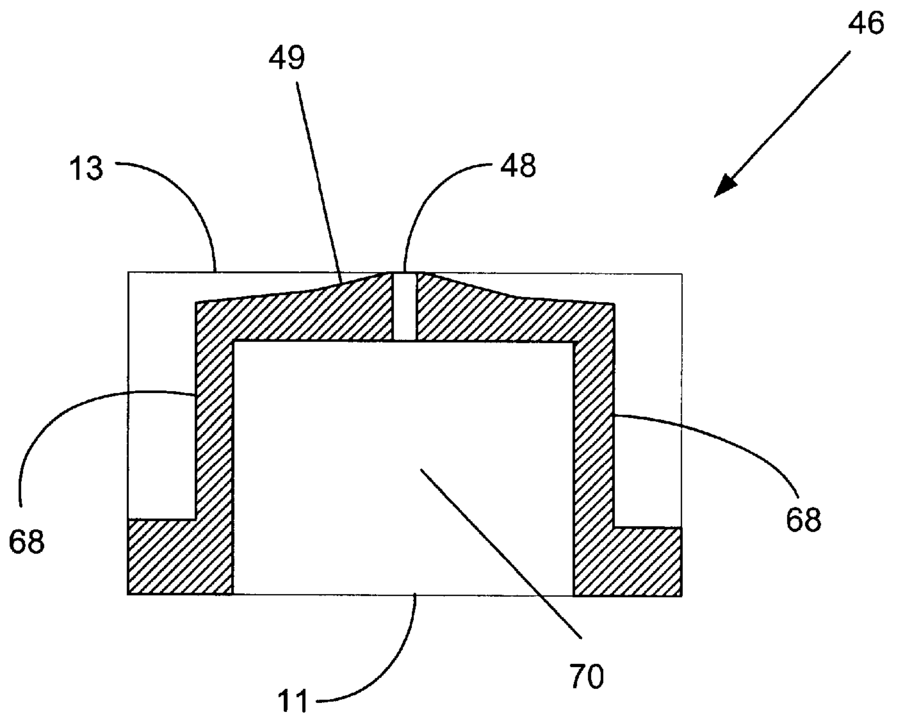
FIGS. 3A and 3B are cross-sectional views of the test array of FIG. 3.

In a preferred embodiment of the present invention as illustrated in FIG. 3 showing the top view of an AST array 12, taken in conjunction with FIG. 2, each AST array 12 comprises a singulated linear row of eight individual microwells 44 connected by the linear microchannel 42 which is formed in the bottom surface 11 of the AST array 12, best seen in FIG. 2. Microchannel 42 is aligned parallel to the row of microwells 44 and is connected to each microwell 44 by a short microchannel 43. Microchannel 42 further connects the microwells 44 to the sacrificial evaporation well 46 disposed between one end of the row of microwells 44 and the inoculum-broth solution receiving reservoir 50. Sacrificial evaporation well 46 may be seen in cross-section view A—A of FIG. 3 seen in FIG. 3A and in FIG. 2B (upwards view from bottom) as comprising a pair of mutually opposed parallel endwalls 68 connected by a pair of mutually opposed parallel sidewalls 72. Endwalls 68 are shorter than sidewalls 72 and endwalls 68 and sidewalls 72 are substantially perpendicular to the bottom surface 11 of test array 12. The upper surfaces of endwalls 68 and sidewalls 72 are connected by a cone-shaped upper surface 49 to form a small generally rectangular evaporation chamber 70 enclosed by sacrificial well 46. An important feature of sacrificial well 46 is the sealable vacuum port 48 formed as an opening in the cone-shaped upper surface 49 that enables air to be evacuated from sacrificial well 46 and to be evacuated from microchannels 42 and 43 and be evacuated from microwells 44 during an inoculum-broth filling operation described hereinafter. Evaporation chamber 70 is typically sized to accommodate an amount of inoculum-broth solution in the 0.02 to 0.04 mL range.

Figure 3B:
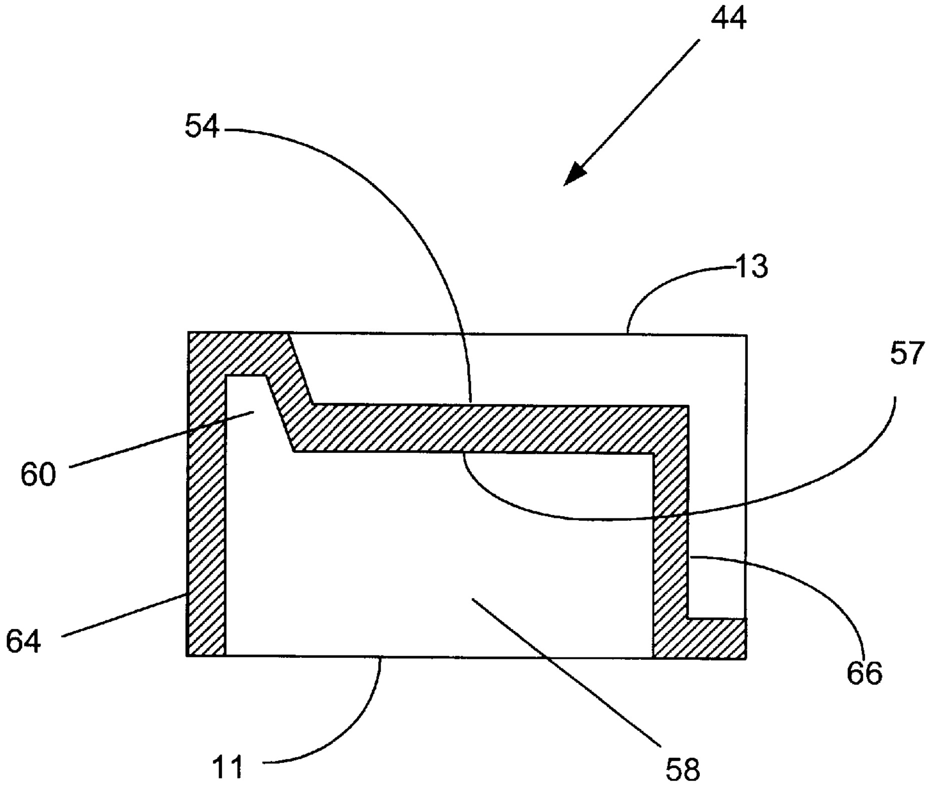

Cross-section B—B in FIG. 3B illustrates the microwells 44 as having a solid irregular top surface 54 portion of array 12, a rounded endwall portion 66 (also see FIG. 2A) of the sidewall 17, a flat endwall portion 64 (also see FIG. 2A) of the indented sidewall 15 and two parallel sidewalls 62. Both endwalls 66 and 64 are formed substantially perpendicular to the lower bottom surface 11 of array 12 and are separated by the two parallel sidewalls 62. The irregular top surface, the flat endwall portion 64, and the rounded endwall portion 66 cooperate to define a small AST test chamber 58. The irregular top surface 54 is shaped to form a recessed top edge portion of AST test chamber 58 adapted to act as a bubble trap 60 for bubbles that may be generated as a inoculum-broth solution is dispensed through microchannel 42 from reservoir 50 to all test microwells 44 in an array 12. It has been unexpectedly found that when microwell 44 is shaped as described herein, then if the microchannel 43 is positioned on the opposite surface of microwell 44 across from the bubble trap 60, the bubble trap 60 is effective in capturing bubbles when microwell 44 is comprised of a generally hydrophilic material, like styrene. It has been observed that with such an arrangement, as inoculum-broth solution flows into microwell 44, any air remaining within microwell 44 is urged by the expanding inoculum-broth solution without leaving any entrapped air pockets in the critical upper central area of the test chamber 58. Such a filling is pictorially illustrated in FIGS. 6A–6D. Thus, air is removed away from the central area of the top surface 54 through which a beam of interrogating radiation may pass as described hereinafter without requiring bubble traps separate from the chamber 58 or bubble traps with complex valve features.

AST test chamber 58 is typically sized to accommodate an amount of inoculum-broth solution in the 0.03 to 0.04 mL range. As also seen in FIG. 2A, each microwell 44 has a generally elongate shaped lateral cross-section with two parallel sidewalls 62, the generally flat endwall portion 64 perpendicular between the parallel sidewalls 62 and the generally rounded front wall 66 also between the two parallel sidewalls 62. In a preferred embodiment, the upper top surface 13 and lower bottom surface 11 are about 0.3–0.4 inches wide, the indented sidewall 15 is about 0.2–0.25 inches in height and the elongate dimension of the test array 12 is about 2.5–3.0 inches in length. In such an embodiment, the microchannel 42 would be sized with a width and depth of about 0.010 to 0.020 inches.

The sacrificial evaporation well 46 is designed to accomplish two important purposes: firstly, provision of a evaporation chamber 70 from which sacrificial evaporation of inoculum-broth solutions may take place, thereby inhibiting evaporation of solution from microwells 44. Evaporation from microwells 44 is inhibited because evaporation initially must occur from within microchannel 53 and then from the sacrificial evaporation chamber 70 before evaporation might occur from microchannels 42 and 43 and microwells 44. Evaporation chamber 70 further provides the sealable vacuum port 48 through which air contained within microwells 44 may be evacuated so that air within microwells 44 does not bubble through broth in the reservoir 50 during evacuation and generate air bubbles within inoculum-broth solutions. After evacuation, sealable vacuum port 48 subsequently sealed so as to generate a flow of inoculum-broth solution from reservoir 50 into the microwells 44.

To fill the microwells 44 with an inoculum-broth solution to be tested, pipetting system 26 dispenses a predetermined quantity of inoculum-broth solution into a reservoir 50 for each AST test array carried on AST array carrier 30 at inoculum-broth dispensing station 28. When all of the reservoirs 50 have been loaded with inoculum-broth solution, transport system 16 shuttles the AST array carrier 30 to AST array vacuum filling station 34 where a clam-shell like vacuum chamber is lowered over the AST array carrier 30 and a vacuum is applied to all AST test arrays 12 carried thereon. When vacuum is applied around the test arrays 12, air is removed from all AST microwells 44 through the sealable vacuum port 48 which is in fluid communication with individual AST microwells 44 by means of microchannels 42 and 43. Subsequent to this evacuation process, a source of heat, for example a previously heated bar having hot-feet portions or an electrical-resistant wire supported within the vacuum chamber may be brought in contact with vacuum port 48 and heated by electrical current for a predetermined time to seal or close port 48 against air flow when vacuum is released; once port 48 is sealed, the vacuum is released within the vacuum chamber. Atmospheric pressure over the inoculum-broth solution in reservoir 50 causes inoculum-broth solution to flow through opening 52 into microchannels 41, 42 and 43 thereby filling the evaporation well 46 and into all microwells 44 in each of the AST test arrays carried by AST array carrier 30. As the microwells 44 are filled with inoculum-broth solution, all remaining air trapped within the chamber 58 will flow into the small recessed top edge portion 60 which acts as a bubble trap within microwell 44.

Preferably, the AST test array 12 is constructed of a molded plastic material, but other types of material can be used. Most preferably, the material used in constructing array 12 is generally translucent, so as to allow uninterrupted transmission of light through microwells 44 during AST testing in the microbiological analyzer 10. As seen in FIG. 3, array 12 further includes a protrusion 76 formed in the sidewall 17, the protrusion 76 being generally shaped as a bulge extending from the body of the array 12 and formed in the uppermost portion of the sidewall 17. The protrusion 76 is used to facilitate loading and retention of an AST array 12 within the AST array carrier 30 and in an exemplary embodiment has dimensions of about 0.26–0.30 mm extension outward from the body of array 12, about 3–4 mm length along the edge of the array 12 and about 0.6–0.8 mm depth along the sidewall 17 of the array 12. Alternately, a high friction material such as silica or an inert powder may be coated onto the side of array 12 in place of protrusion 76 to accomplish a similar function.

AST testing may conveniently be accomplished by directing a beam of interrogating radiation from above or below each AST array 12 through the central arc portion 56 of the top surface 54 of each microwell 44 and measuring the degree of absorption or change in color or generation of a fluorescent signal using a calorimetric or fluorometric photodetector located below or above each microwell 44. For this reason, the upper center portion 56 of the top surface 54 of every microwell 44 (best seen in FIG. 3) and the lower center portion 57 of the top surface 54 of every microwell 44 are molded so as to have a surface finish smoothness equivalent to or more smooth than SPI #A-1 grade #3 diamond buff in order to minimize optical interference during AST testing.

It is to be understood that the embodiments of the invention disclosed herein are illustrative of the principles of the invention and that other modifications may be employed which are still within the scope of the invention. Accordingly, the present invention is not limited to those embodiments precisely shown and described in the specification but only by the following claims.

What is claimed is:

1. A test array adapted for antibiotic susceptibility testing of microorganisms comprising:

an elongate shaped body with opposed and parallel top and bottom surfaces separated by a generally flat sidewall and an opposed generally indented sidewall, said body having a length and a plurality of upwardly projecting microwells formed in the lower surface as a linear row of single microwells parallel to said length;

an open solution receiving reservoir formed in the top surface of the test array;

a sacrificial evaporation well formed in the bottom surface of the test array upwardly projecting from an open portion of the bottom surface and disposed between the row of microwells and the reservoir;

an open first microchannel formed in the bottom surface of the elongate body and connecting each microwell to the sacrificial evaporation well; and an open second microchannel formed in the bottom surface of the elongate body and connecting the sacrificial evaporation well to the solution receiving reservoir.

2. The test array of claim 1 wherein the sacrificial evaporation well has an upper closed portion proximate the top surface of the test array, the upper portion having a heat sealable air vent port formed therein.

3. The test array of claim 1 wherein the test array is formed of a generally translucent material and the upper and lower center portions of the top surface of each microwell are molded in a manner that produces a smooth surface finish on said center portions.

4. The test array of claim 3 wherein the surface finish smoothness is equivalent to or more smooth than SPI #A-1 grade #3 diamond buff.

5. The test array of claim 1 further comprising a retaining protrusion formed in the generally flat sidewall, the protrusion being generally shaped as a bulge extending outwards from the array.

6. The test array of claim 5 wherein the retaining protrusion has dimensions of about 0.26–0.30 mm extension outward from the array, about 3–4 mm along the length of the array and about 0.6–0.8 mm depth along the generally flat sidewall of the array.

7. The test array of claim 1 wherein the number of upwardly projecting microwells is eight and each microwell forms a test chamber sized to accommodate an amount of liquid solution in the 0.5 to 0.9 mL range.

8. The test array of claim 1 wherein the sacrificial evaporation well is sized to accommodate an amount of liquid solution in the in the 0.02 to 0.04 mL range.

9. The test array of claim 1 wherein the top surface and bottom surface are about 0.3–0.4 inches wide, the opposed sidewalls are about 0.2–0.25 inches in height and the array has an overall elongate length of about 2.5–3.0 inches.

10. The test array of claim 1 wherein the first microchannel has an approximate width and depth of about 0.010 to 0.020 inches.

* * * * *